(12) United States Patent
Kopperschmidt

(10) Patent No.: US 10,744,466 B2
(45) Date of Patent: Aug. 18, 2020

(54) METHOD FOR BLOWING FREE A WETTED HYDROPHOBIC FILTER, AND DEVICE FOR CARRYING OUT THE METHOD

(75) Inventor: Pascal Kopperschmidt, Dittelbrunn (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 1540 days.

(21) Appl. No.: 12/085,680

(22) PCT Filed: Jul. 14, 2006

(86) PCT No.: PCT/EP2006/006912
§ 371 (c)(1),
(2), (4) Date: May 29, 2008

(87) PCT Pub. No.: WO2007/065490
PCT Pub. Date: Jun. 14, 2007

(65) Prior Publication Data
US 2009/0152179 A1 Jun. 18, 2009

(30) Foreign Application Priority Data
Dec. 5, 2005 (DE) .......... 10 2005 058 012

(51) Int. Cl.
*B01D 35/14* (2006.01)
*B01D 35/143* (2006.01)
(Continued)

(52) U.S. Cl.
CPC .......... *B01D 65/10* (2013.01); *A61M 1/3639* (2013.01); *A61M 1/3641* (2014.02); *B01D 65/02* (2013.01);
(Continued)

(58) Field of Classification Search
CPC ........ A61M 2205/7554; A61M 1/3639; A61M 1/3641
(Continued)

(56) References Cited

U.S. PATENT DOCUMENTS 3,964,479 A * 6/1976 Boag .................. A61M 1/3627
604/123
4,345,999 A * 8/1982 Sigdell et al. ...................... 96/6
(Continued)

FOREIGN PATENT DOCUMENTS

DE 35 43 126 A1 6/1986
EP 0 330 761 A1 9/1989
(Continued)

OTHER PUBLICATIONS

Oxford Dictionary, "The Concise Oxford Dictionary," 10th ed., ed. Judy Pearsall, pub. Oxford University Press, New York, 1999, 3 pages.*
(Continued)

*Primary Examiner* — Bobby Ramdhanie
*Assistant Examiner* — Denise R. Anderson
(74) *Attorney, Agent, or Firm* — Jacobson Holman, PLLC

(57) ABSTRACT

A method for clearing a wetted hydrophobic filter includes a first step in which the air permeability of the hydrophobic filter is monitored, and a second step in which the hydrophobic filter is cleared by means of a connected air pump, if it is detected that the hydrophobic filter is clogged. An apparatus for performing this method includes a pressure sensor and an air pump connected to an air separation chamber via a conduit, and a control and monitoring unit configured to actuate the air pump in order to clear the hydrophobic filter.

10 Claims, 1 Drawing Sheet

(51) Int. Cl.
  *B01D 65/10* (2006.01)
  *A61M 1/36* (2006.01)
  *B01D 65/02* (2006.01)

(52) U.S. Cl.
  CPC .............. *A61M 2205/7554* (2013.01); *B01D 2321/185* (2013.01); *B01D 2325/38* (2013.01)

(58) Field of Classification Search
  USPC ........................................................ 210/90
  See application file for complete search history.

(56) References Cited

U.S. PATENT DOCUMENTS

| | | | | |
|---|---|---|---|---|
| 4,907,166 | A | * | 3/1990 | Corenman et al. .............. 702/30 |
| 4,919,817 | A | * | 4/1990 | Schoendorfer ......... A61M 1/34 210/321.68 |
| 5,227,049 | A | * | 7/1993 | Chevallet et al. .............. 210/97 |
| 5,643,455 | A | | 7/1997 | Kopp et al. |
| 5,808,181 | A | * | 9/1998 | Wamsiedler et al. .............. 73/38 |
| 6,187,207 | B1 | * | 2/2001 | Brauer .......................... 210/739 |
| 6,306,291 | B1 | * | 10/2001 | Lueck .............................. 210/90 |

FOREIGN PATENT DOCUMENTS

| | | | | |
|---|---|---|---|---|
| EP | 0330761 | * | 9/1989 | .......... A61M 1/3639 |
| EP | 0330761 A1 | * | 9/1989 | .......... A61M 1/1601 |
| EP | 1 319 417 A1 | | 6/2003 | |
| EP | 1 547 630 A1 | | 6/2005 | |
| WO | WO 2004/000391 A1 | | 12/2003 | |

OTHER PUBLICATIONS

Oxford Dictionary, "The Concise Oxford Dictionary," 10$^{th}$ ed., ed. Judy Pearsall, pub. Oxford University Press, New York, 1999, 4 pages.*

* cited by examiner

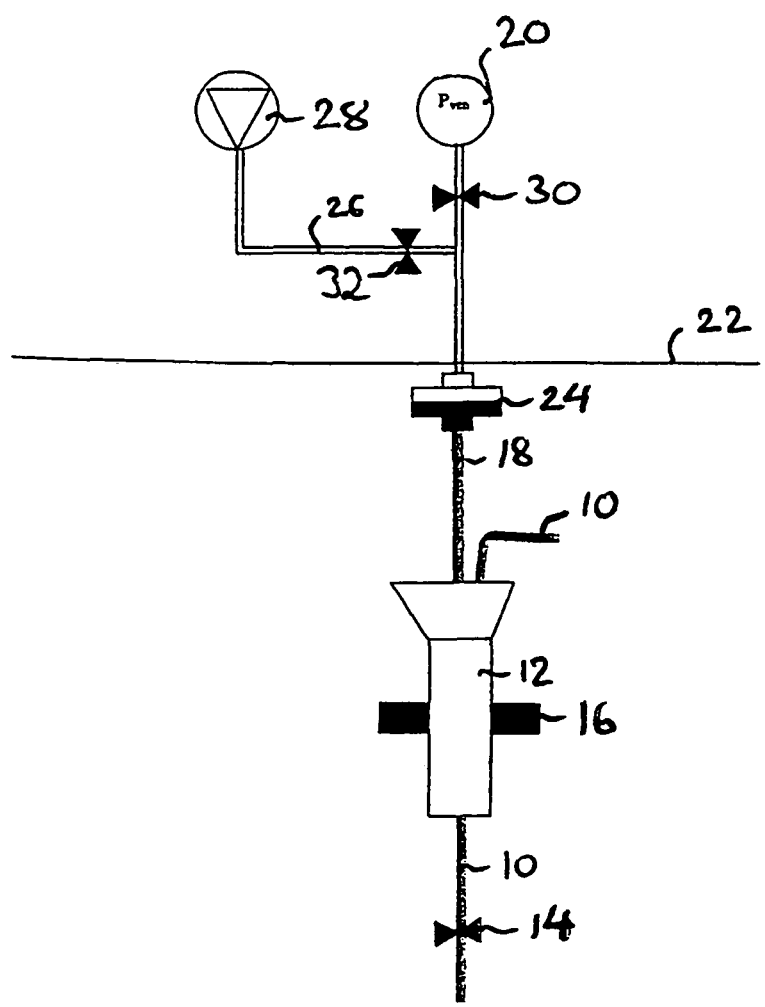

METHOD FOR BLOWING FREE A WETTED HYDROPHOBIC FILTER, AND DEVICE FOR CARRYING OUT THE METHOD

This is a national stage of PCT/EP2006/006912 filed Jul. 14, 2006 and published in German.

Cross-Reference To Related Application

BACKGROUND OF THE INVENTION

1. Field of Invention

This invention relates to a method of clearing a wetted hydrophobic filter and an apparatus for performing this method.

2. Description of the Prior Art

It is known already to connect a pressure sensor in an extracorporeal blood circulation via a tube conduit branching off from this blood circulation, in order to measure the pressure in this blood circulation. In principle, this connecting conduit can branch off at any point of the blood circulation, for instance from a venous air separation chamber present in the blood circulation.

In the branching tube, to which the pressure sensor is connected, a certain amount of air is included, by means of which the pressure is transferred to the pressure sensor. Usually, the pressure sensor is integrated in a blood treatment machine. To prevent the undesired advancement of blood up to the blood treatment machine, at least one hydrophobic protective filter is disposed in the conduit. Together with the remaining set of blood tubes of the extracorporeal blood circulation, this hydrophobic filter is discarded upon completion of a blood treatment.

During operation of the extracorporeal blood circulation, it can occur that the hydrophobic filter is wetted by the blood and thereby is at least partly clogged unilaterally. This results in a—partly creeping—impairment of the operability of the pressure measurement. This problem is discussed in EP-A-0 330 761. To be able to detect the malfunction, according to this teaching, the pressure sensor should not only detect the static pressure, but there should also be detected the pressure fluctuations present in the extracorporeal blood circulation. As far as the pressure sensor system becomes less sensitive, it is not only the static pressure which no longer is indicated correctly, but the periodic pressure fluctuations no longer are indicated either. If the pressure fluctuations no longer can regularly be detected by the pressure sensor, it can be concluded that the hydrophobic filter is clogged to such an extent that a sufficiently precise pressure measurement no longer is possible.

As far as the user recognizes this problem, he can destroy the filter in a controlled way and replace the same by a second filter. In general, however, the hydrophobic filter is connected with the entire set of blood tubes, so that a filter change only is possible with a considerable effort.

From U.S. Pat. No. 3,964,479 there is already known an extracorporeal blood circulation, in which a pressure sensor is connected to a branching point of an air separation chamber provided in the blood circulation. The teaching of this U.S. patent deals with the problem of adjusting liquid levels inside the air separation chamber at a desired height. For this purpose, an air pump is branched off from the conduit between the air separation chamber and the pressure sensor, in which a hydrophobic filter is also provided according to the known solution, which air pump serves to set the liquid level in the air separation chamber at a certain level. For this purpose, air can be pumped into the air separation chamber or be withdrawn from the same.

SUMMARY OF THE INVENTION

It is the object of the present invention to propose a method and an apparatus which upon detection of a clogged filter eliminates such malfunction automatically, if possible, and at least leads to the fact that the hydrophobic filters must be replaced less frequently.

In accordance with the invention, this object is solved by the combination of the features described herein. In accordance with the invention, there is created a method for clearing a wetted hydrophobic filter in an extracorporeal blood circulation, wherein the extracorporeal blood circulation includes an air separation chamber to which a pressure pick-up and an air pump are connected via a conduit, the hydrophobic filter being disposed within said conduit. The method of the invention at least comprises the following steps:

monitoring the air permeability of the hydrophobic filter, and clearing the hydrophobic filter by means of the connected air pump, if it is detected that the hydrophobic filter is clogged.

Monitoring the air permeability of the hydrophobic filter can for instance be effected analogous to the above-mentioned teaching in accordance with EP-A-0 330 761. If an at least partial clogging of the hydrophobic filter is detected, the connected air pump is actuated via a corresponding control such that the hydrophobic filter is cleared.

A preferred aspect of this teaching of the invention is disclosed herein.

Accordingly, the air permeability of the hydrophobic filter can be monitored by means of the pressure pick-up.

While the hydrophobic filter is cleared, a clamp disposed in the extracorporeal blood circulation downstream of the air separation chamber can be opened on the one hand, and on the other hand valves can be opened, which are provided in the connecting conduits to the air pump and to the pressure pick-up.

Advantageously, the course of pressure over time is adopted by the air pump during the clearing process.

When the change in pressure per unit time, i.e. the rate of change in pressure, exceeds a specified limit value, an alarm signal for replacing the hydrophobic filter is produced. Then, clearing definitely is not easily possible. It should be considered that the blow rate of the air pump cannot be increased to any extent, as in a borderline case the bursting pressure of the hydrophobic filter will be exceeded.

However, if the change in pressure per unit time does not exceed the specified limit value, the valve in the supply conduit of the air pump can advantageously be closed again upon clearing the filter.

In accordance with another advantageous aspect of the invention, the filling level of the blood in the air separation chamber is monitored by means of a filling level detector during the clearing process. It can thus be prevented that the filling level decreases too much and, in an extreme case, air gets into the tube system and hence into the patient.

Advantageously, the air pump is actuated by means of a control and monitoring program which also records the pressure values over time.

An apparatus for performing the method of the invention is disclosed in claim 9. This apparatus includes an air separation chamber disposed in an extracorporeal blood circulation, to which a pressure pick-up and an air pump for adjusting the filling level in the air separation chamber are connected via a conduit, a hydrophobic filter being provided in said conduit. For performing the aforementioned method, this apparatus includes a control and monitoring unit by means of which the air pump can be actuated for clearing the hydrophobic filter, while at the same time the pressure values per unit time can be recorded and monitored.

Furthermore, the apparatus for performing the method of the invention preferably includes an alarm device for producing an alarm for the case that the hydrophobic filter cannot be cleared.

BRIEF DESCRIPTION OF THE DRAWINGS

Further features, details and advantages of the invention will be explained with reference to the embodiment illustrated in the sole drawing FIGURE. The sole FIGURE shows a schematic representation of a part of an extracorporeal blood circulation.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the representation as shown in the FIGURE, only part of a blood-carrying tube or conduit 10 of an extracorporeal blood circulation is shown, which extends from the top into a conventionally designed air separation chamber 12 and then extends from the lower end of the air separation chamber 12. The air separation chamber 12 can be disposed for instance in the blood return conduit (venous blood conduit) of the extracorporeal blood circulation. Below the air separation chamber 12, a pinch clamp 14 is disposed in the blood-carrying tube or conduit 10. For detecting the filling level of the blood inside the air separation chamber 12, a filling level detector 16 is mounted on the air separation chamber 12.

Via an air-carrying tube or conduit 18, the air separation chamber 12 is connected with a pressure sensor 20. The pressure sensor 20 is disposed inside a dialysis device, whose outer wall is only indicated here by the line 22 for the sake of simplification. In the air-carrying tube or conduit 18 between the air separation chamber 12 and the pressure sensor 20, a hydrophobic filter 24 is disposed still outside the dialysis device.

Inside the dialysis device, a conduit 26 leading to an air pump 28 branches off from the air-carrying tube or conduit 18. Between the branching point to the conduit 26 and the pressure sensor 20, the air-carrying tube or conduit 18 includes a controllable valve 30. The air-carrying conduit 26 likewise includes a controllable valve 32.

During the usual operation of the extracorporeal blood circulation, blood is dripping from the blood-carrying tube or conduit 10 into the air separation chamber 12. The filling level in the air separation chamber 12 is monitored by means of the filling level detector 16. If the level falls below a desired level, the height of the filling level of the blood in the air separation chamber 12 can be adjusted here by means of the air pump 28 or the pinch clamp 14. During the operation of the extracorporeal blood circulation, the pressure is determined by the pressure sensor 20. Via a measurement routine, as it is known for instance from EP-A-0 330 761, it can be detected here whether the hydrophobic filter 24 is at least partly clogged due to wetting with blood. If a partial clogging is detected, the valves 30 and 32 are opened (unless the valve 30 has already been open), and by means of the air pump 28 an excess pressure is produced, in order to clear the hydrophobic filter 24. During such clearing, the pinch clamp 14 is opened at the same time (unless it has already been open), in order to avoid an excess pressure in the system.

While air is supplied to the hydrophobic filter 24, the course of pressure over time is monitored by means of the pressure sensor. Should the pressure rise too fast, this indicates a fundamental problem inside the filter, which cannot be overcome by clearing by means of the air pump 28. In this case, an alarm signal is activated by the control and monitoring means, which is provided to the user by a corresponding alarm device. In the case of an alarm, the hydrophobic filter 24 must be replaced.

Should the increase in pressure be small enough, clearing is possible. In this case, it must merely be ensured by means of the level detector 16 that the blood level inside the venous air separation chamber 12 does not decrease too much, in order to safely prevent the penetration of air into the blood-carrying tube or conduit 10 inside the air separation chamber 12.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of clearing a wetted hydrophobic filter in an extracorporeal blood circulation having an air separation chamber to which a pressure sensor and an air pump are connected via a conduit having the wetted hydrophobic filter disposed therein, said method comprising the following steps:

monitoring an air permeability of the wetted hydrophobic filter with the pressure sensor for detecting whether the wetted hydrophobic filter is clogged, the pressure sensor being located so as to determine a pressure in the conduit connecting the air pump and the wetted hydrophobic filter;

if the monitoring step determines that the wetted hydrophobic filter is clogged, supplying air from the air pump to the wetted hydrophobic filter so as to clear the wetted hydrophobic filter;

while the air is supplied from the air pump to the wetted hydrophobic filter, monitoring with the pressure sensor a change of pressure per unit time in the conduit; and if the change of pressure per unit time exceeds a specified limit value, producing an alarm signal for replacing the wetted hydrophobic filter.

2. The method according to claim 1, further comprising the step of during the step of supplying the air from the air pump to the wetted hydrophobic filter for clearing the wetted hydrophobic filter, opening a clamp disposed in the extracorporeal blood circulation downstream of the air separation chamber.

3. The method according to claim 1, further comprising the step of if the change of pressure per unit time does not exceed the specified limit value, stopping the supply of the air from the air pump again upon clearing the wetted hydrophobic filter.

4. The method according to claim 1, further comprising the step of
monitoring a filling level of blood in the air separation chamber with a filling level detector.

5. The method according to claim 1, wherein the air pump is actuated by a control and monitoring program, the control and monitoring program recording pressure values over time.

6. The method according to claim 1, further comprising the steps of
monitoring a static pressure with the pressure sensor;
in the step of monitoring the air permeability of the wetted hydrophobic filter with the pressure sensor, monitoring pressure fluctuations; and
concluding that the wetted hydrophobic filter is clogged if the pressure fluctuations are not regularly detected by the pressure sensor.

7. An apparatus for clearing a wetted hydrophobic filter in an extracorporeal blood circulation, said apparatus comprising:
an air separation chamber disposed in the extracorporeal blood circulation, to which a pressure sensor and an air pump are connected via a conduit having the wetted hydrophobic filter disposed therein, with the pressure sensor being located so as to determine a pressure in the conduit connecting the air pump and the wetted hydrophobic filter, and
a control and monitoring unit configured for
monitoring an air permeability of the wetted hydrophobic filter with the pressure sensor for detecting whether the wetted hydrophobic filter is clogged;
actuating the air pump for supplying air to the wetted hydrophobic filter for clearing the wetted hydrophobic filter if the monitoring step determines that the wetted hydrophobic filter is clogged,
while the air is supplied from the air pump to the wetted hydrophobic filter, monitoring with the pressure sensor a change of pressure per unit time in the conduit; and
actuating an alarm device that produces an alarm signal for replacing the wetted hydrophobic filter if the change of pressure per unit time exceeds a specified limit value.

8. The apparatus according to claim 7, wherein the control and monitoring unit is further configured for
stopping the supply of the air from the air pump again upon clearing the wetted hydrophobic filter if the change of pressure per unit time does not exceed the specified limit value.

9. The apparatus according to claim 8, wherein the control and monitoring unit is further configured for
monitoring a static pressure with the pressure sensor;
monitoring the air permeability of the wetted hydrophobic filter with the pressure sensor, monitoring pressure fluctuations; and
concluding that the wetted hydrophobic filter is clogged if the pressure fluctuations are not regularly detected by the pressure sensor.

10. An apparatus for clearing a wetted hydrophobic filter in an extracorporeal blood circulation, said apparatus comprising:
an air separation chamber disposed in the extracorporeal blood circulation, to which a pressure sensor and an air pump are connected via a conduit having the wetted hydrophobic filter disposed therein, with the pressure sensor being located so as to determine a pressure in the conduit connecting the air pump and the wetted hydrophobic filter, and
a control and monitoring unit configured for
monitoring a static pressure with the pressure sensor;
monitoring pressure fluctuations;
if the pressure fluctuations are not regularly detected by the pressure sensor, actuating the air pump for supplying air to the wetted hydrophobic filter for clearing the wetted hydrophobic filter,
while the air is supplied from the air pump to the wetted hydrophobic filter, monitoring with the pressure sensor a change of pressure per unit time in the conduit; and
actuating an alarm device that produces an alarm signal for replacing the wetted hydrophobic filter if the change of pressure per unittime exceeds a specified limit value; and
stopping the supply of the air from the air pump again upon clearing the wetted hydrophobic filter if the change of pressure per unit time does not exceed the specified limit value.

\* \* \* \* \*